United States Patent

Hruby et al.

[11] Patent Number: 4,457,864
[45] Date of Patent: Jul. 3, 1984

[54] SYNTHETIC ANALOGUES OF α-MELANOTROPIN

[75] Inventors: Victor J. Hruby; Mac E. Hadley; Christopher B. Heward, all of Tuscon, Ariz.; Tomi K. Sawyer, Kalamazoo, Mich.

[73] Assignee: University Patents, Inc., Norwalk, Conn.

[21] Appl. No.: 314,387

[22] Filed: Oct. 23, 1981

[51] Int. Cl.$^3$ ............................................. C07C 103/52
[52] U.S. Cl. ............................................. 260/112.5 R
[58] Field of Search ............................. 260/112.5 R

[56] References Cited

PUBLICATIONS

Chem. Abstr., vol. 77, (1972), 165060x.
Chem. Abstr., vol. 67, (1967), 97351j.
Chem. Abstr., vol. 70, (1969), 4601q.
Chem. Abstr., vol. 95, (1981), 144240n.
J. A. Parsons, Peptide Hormones, Ch. I, pp. 1–7.

Primary Examiner—Delbert R. Phillips
Attorney, Agent, or Firm—Marshall, O'Toole, Gerstein, Murray & Bicknell

[57] ABSTRACT

Analogues of the tridecapeptide hormone, α-melanotropin (α-melanocyte stimulating hormone, α-MSH) of the formula:

$$\text{Ac-Ser}^1\text{-Tyr}^2\text{-Ser}^3\text{-Y}^4\text{-Glu}^5\text{-His}^6\text{-X}^7\text{-Arg}^8\text{-Trp}^9\text{-Gly}^{10}\text{-Lys}^{11}\text{-Pro}^{12}\text{-Val}^{13}\text{-NH}_2$$

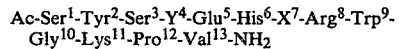

wherein X and Y are amino acid residues and X is in a D-isomeric configuration. Preferred analogues, e.g. [Nle$^4$, D-Phe$^7$]-α-MSH, display increased in vitro and in vivo potency, prolongation and serum stability characteristics and may be covalently bonded to other elements or compounds (e.g., radioisotopes of iodine) without significant loss of biological activity.

3 Claims, 3 Drawing Figures

SYNTHETIC ANALOGUES OF α-MELANOTROPIN

BACKGROUND OF THE INVENTION

The present invention relates generally to synthetic analogues of the tridecapeptide hormone α-melanotropin and more particularly to analogues which exhibit increased potency, prolongation and serum stability characteristics in comparison to the native hormone and which retain biological activity when covalently bonded to other elements or compounds.

α-Melanotropin (α-MSH, α-melanocyte stimulating hormone) is a tridecapeptide synthesized and secreted by the pars intermedia of the vertebrate pituitary. By convention, the amino acid residues of this tridecapeptide are numbered sequentially from the amino terminal (here acetyl substituted) carbon atom through the carboxy terminal (here carboxamide terminal) as follows:

In this formula the following abbreviations are used: Ser=serine; Tyr=tyrosine; Met=methionine; Glu=glutamic acid; His=histidine; Phe=phenylalanine; Arg=arginine; Trp=tryptophan; Gly=glycine; Lys=lysine; Pro=proline; Val=valine.

α-MSH reversibly darkens amphibian skins by stimulating melanosome movement (dispersion) within melanophores. α-Melanotropin also affects both normal and transformed (melanoma) mammalian melanocytes by stimulating adenylate cyclase activity, tyrosinase activity and melanin production. In addition, recent studies suggest that the native hormone may have important functions in fetal development and in neural mechanisms related to learning and memory. See, *Front. Horm. Res.*, 4, (Tilders, et al., Eds.), S. Karger, Basil (1977).

The recognition that α-MSH functions in a number of roles in mammals, including humans, in addition to its well-characterized role in the color change mechanism of poikilothermic vertebrates and its effect on melanoma cell activity and growth, has prompted substantial research into production and testing of synthetic α-MSH and analogues thereof.

Variation in biological effects of α-MSH analogues are generally discussed in terms of "potentiation" (increased activity relative to naturally-occurring α-MSH) and "prolongation". Such effects are measured by the classic frog skin bioassay system. See, Shizume, et al., *Endocrinology*, 54, 553-560 (1954). Because α-MSH has an extremely short half-life in serum (about 2 minutes), synthetic analogues having greater serum stability in addition to greater potency and prolongation characteristics have been sought. Finally, because the hormone is essentially inactivated upon attempted iodination for purposes of generating a radiolabelled compound synthetic analogues capable of retaining biological activity after such processing have also been sought.

Of particular interest to the background of the invention are early studies noting the effects of heat-alkali treatment of naturally-isolated and synthetic α-MSH. Briefly put, products of such treatment lost optical activity due to varying degrees of randomized racemization of amino acids from L- to D-isomeric configurations. The treated hormones, however, exhibited significantly prolonged and retarded biological activities. It has been reported, for example, that in vivo and in vitro treatment of frog skins with heat-alkali treated α-MSH, β-MSH or ACTH resulted in prolonged melanotropic (skin darkening) activity. Maximum prolongation and potentiation for α-MSH resulted when the hormone was heated at 60° C. for 40 minutes in a solution of 0.1 N NaOH, and it was implicitly assumed that the biological effect was due to racemization of one or more residues in the peptide. See, e.g., Geschwind, et al. *Arch. Biochem. Biophys.*, 106, pp. 200-206 (1964); Lerner et al, *Exerpta Medica Int. Congr. Series* 83, pp. 392-397 (1964); and Lande, et al., *Biochem. Biophys. Acta*, 251, pp. 246-253 (1971). As long ago as 1967 it was noted that: "It is important that α-MSH be made with D-amino acids in one or two places. If the site of racemization can be pinpointed, it may be possible to produce well-characterized peptides more active than the natural hormone" [Lande, et al., *Pharm. Rev.*, 19, pp. 1-20 (1967)].

Research consistent with such suggestions, however, has provided less than satisfactory results. As one example, the synthetic analogue of α-MSH containing L-configuration amino acids at all but position 2 (i.e., [D-Tyr²]-α-MSH) was found to be significantly less potent than the natural hormone. See, Sawyer, et al., "Peptides: Structure and Biological Function," *Proc. 6th Am. Pept. Symp.* (Gross, et al., eds.) pp. 1017-1020, Pierce Chem. Co., Rockford, Ill. (1979). Similarly, it has been reported that the synthetic analogue of α-MSH containing D-Ser¹ was no more active than the native hormone. See, Eberle, et al., *Helv. Chim. Acta*, 62, pp. 2460-2483 (1979).

Also of interest to the background of the present invention is the finding that substitution of aliphatic aminoacids such as norleucine (Nle) for methionine at position 4 resulted in more potent biological activity. [Nle⁴]-α-MSH was found to be approximately twice as potent as α-MSH both in dispersing amphibian melanophores and in stimulating melanoma adenylate cyclase activity. See, Sawyer, et al., supra. The Nle⁴ analogue was found to be resistant to inactivation by chloramine-T, an oxidant used in peptide iodination, but was inactivated upon further contact with sodium iodide. See, Heward, et al., *Hoppe-Seyler's Z. Physiol. Chem.*, 360, pp. 1851-1859 (1979).

There continues to exist, therefore, a longstanding need in the art for serum-stable, highly potent α-MSH analogues which have prolonged biological activity and which retain biological activity upon iodination processing.

Specifically incorporated by reference herein for the purpose of illustrating the background of the invention and the prior art is the publication by the inventors and their co-workers appearing in *P.N.A.S.* 77, pp. 5753-5758 (October 24, 1980).

BRIEF SUMMARY

The present invention provides novel synthetic analogues of α-MSH which possess an unexpected combination of high potency, prolonged activity and serum stability while retaining biological activity upon iodination.

The novel compounds according to this invention comprise α-MSH analogues of the formula,

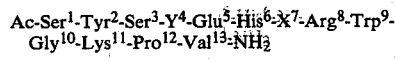

wherein X and Y are amino acid residues, X is in a D-isomeric configuration, and all remaining amino acid residues are in L-isomeric configuration.

Preferred compounds include the [Nle⁴, D-Phe⁷] analogue of α-MSH in which the D-isomeric configuration of phenylalanine (Phe) occupies the "7" position within the tridecapeptide and norleucine (Nle) has been substituted for methionine (Met) at the "4" position.

Also comprehended by the invention are those analogues wherein one, two, or three amino acid residues other than that occupying position 7 are in the D-isomeric configuration.

Analogues of the invention may be easily prepared by the well-known methods used in preparing synthetic α-MSH.

Compounds of the invention are highly potent in vitro stimulators of mouse melanoma adenylate cyclase activity. The compounds are also more potent than α-MSH in both in vitro and in vivo amphibian melanophore bioassays, and, unlike [Nle⁴]-α-MSH and α-MSH, exhibit prolonged biological activity in such systems. Compounds of the invention also exhibit resistance to serum enzyme degradation superior to that of α-MSH and [Nle⁴]-α-MSH. These compounds may also be labelled with radioactive iodine using lacto peroxidase or iodogen without significant loss of biological activity, and, in addition, are not oxidatively inactivated by Chloramine-T treatment.

Numerous aspects and advantages of the present invention will become apparent upon consideration of the following detailed description wherein FIGS. 1 through 3 graphically illustrate biological activity data for a preferred compound of the invention and prior art compounds.

DETAILED DESCRIPTION

The following examples relate to the preparation nd biological activity of D-isomeric α-MSH analogues of the formula

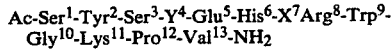

wherein X and Y are amino acid residues, X is in a D-isomeric configuration, and all remaining amino acid residues in the tridecapeptide are in L-isomeric configuration.

More specifically, Examples 1 through 7 illustrate the preparation of [Nle⁴, D-Phe⁷]-α-MSH and its biological properties.

EXAMPLE 1

[Nle⁴, D-Phe⁷]-α-MSH was synthesized by solid phase synthesis and purified according to the method described in Sawyer et. al., *P.N.A.S.* 77, pp. 5754–5758 (1980).

Briefly summarized, the compound was synthesized by first preparing a p-methylbenzhydrylamine resin to which the desired amino acids were coupled successively as their Nα-Boc derivatives. Except for use of norleucine as a substitute for methionine at position 4 and use of D-phenylalanine in place of L-phenylalanine at position 7, all amino acid residues used were identical to those present in native α-MSH and were of the L-isomeric configuration. The reactive side group of each amino acid was protected by incorporation of an appropriate protective group. After all the amino acid residues were coupled to the resin, the amino terminus of the peptide-resin was acetylated. Subsequent to acetylation the protected peptide was cleaved from the resin, and all protecting groups were removed. The crude [Nle⁴, D-Phe⁷]-α-MSH was purified by ion-exchange chromatography and its homogeneity was tested by thin layer chromatography on silica gel using appropriate solvents. Optical rotation values were measured at the mercury-green line (546 nm) in a Perkin-Elmer 241 MC polarimeter.

The following example illustrates the enhanced activity of the compound of Example 1 on melanoma adenylate cyclase activity in mammalian cell cultures. The α-MSH utilized for comparative purposes in this and subsequent examples was prepared as described in Yang, et. al., *Int. J. Pept. Protein Res.* 15, 130–138 (1980). [Nle⁴]-α-MSH, also used for comparative analysis, was either purchased from Penninsula Laboratories (San Carlos, Cal.) or was prepared as described in Hruby, et al., *J. Med. Chem.* 23, pp. 1432–1437 (1980).

EXAMPLE 2

The relative effects of α-MSH, [Nle⁴]-α-MSH and [Nle⁴, D-Phe⁷]-α-MSH on mammalian melanoma adenylate cyclase activity in vitro were determined by assaying [α-³²P] ATP conversion to [³²P]cAMP in Cloudman S-91 mouse melanoma tumors as described in Sawyer, et al., supra. [³²P]cAMP was isolated, purified and dectected according to Salomon et al., *Anal. Biochem.*, 58, pp. 541–48 (1974).

Figure 1:
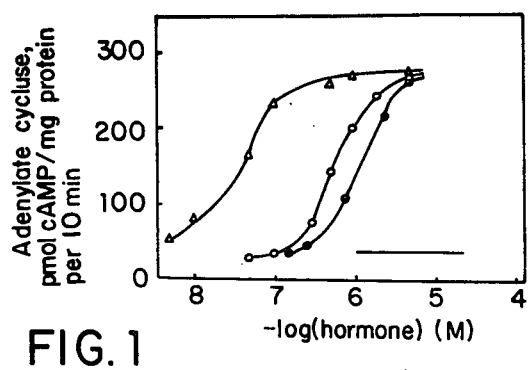

As illustrated in the dose-response curves of FIG. 1, [Nle⁴, D-Phe⁷]-α-MSH (Δ), while exhibiting the same maximal adenylate cyclase activity as α-MSH (●) and [Nle⁴]-α-MSH (0), was significantly more potent than either compound, fully 26 times as potent as the native hormone.

The following example illustrates the in vitro effects of [Nle⁴, D-Phe⁷]-α-MSH on tyrosinase activity in melanoma cells in tissue culture.

EXAMPLE 3

Cloudman S-91 NCTC 3960 (CCL 53.1) melanoma cells were obtained from the American Type Culture Collection Cell Repository and were grown and maintained as described in Fuller, et. al. *Pigment Cell,* 4 pp. 97–104 (1979). Melanoma cells (2×10⁵) were seeded in 25 cm² flasks and allowed to attach overnight. At time t=0, the medium in all the flasks was replaced with 4 ml of medium containing 0.1 μM melanotropin (i.e., α-MSH, [Nle⁴]-α-MSH, or [Nle⁴, D-Phe⁷]-α-MSH) or a control medium containing no melanotropin. At selected time intervals (t=0.5, 4, and 8 hr.) the control medium and melanotropin-containing medium was removed. The cells were carefully rinsed three times with fresh melanotropin-free medium and then exposed to fresh melanotropinfree medium containing [³H]-tyrosine (specific activity 48 Ci/mmol; 1 Ci=3.7×10¹⁰ becquerels) at 1 μCi/ml. After 24 hr, this medium was removed and the tyrosinase activity of the melanoma cells was determined by assaying for the ³H₂O released from the [³H]tyrosine by the action of tyrosinase.

Figure 2:
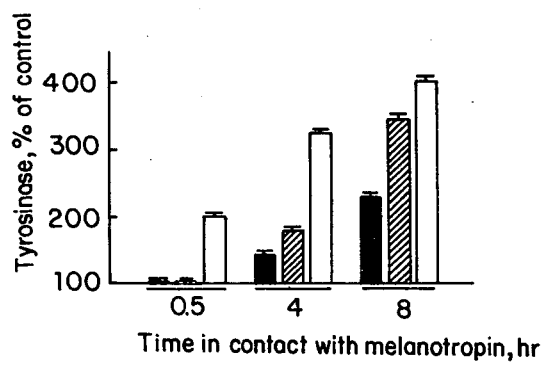

As illustrated in FIG. 2, [Nle⁴, D-Phe⁷]-α-MSH (empty bars) was found to be much more active than α-MSH (filled bars) or its norleucine analogue, [Nle⁴]-α-MSH (hatched bars). Tyrosinase activities are expressed as percent activity of control cells (i.e., cells not exposed to melanotropin). Each bar represents the mean of four determinations ±SEM.

The following examples illustrate, respectively, the in vitro and in vivo effects of [Nle$^4$, D-Phe$^7$]-α-MSH on melanosome dispersion.

EXAMPLE 4

[Nle$^4$, D-Phe$^7$]-α-MSH was examined with respect to the duration of its ability to stimulate melanosome dispersion in vitro using the frog (*Rana pipiens*) skin bioassay as described in Shizume, *Endocrinology* 54, 553-560 (1954).

The [Nle$^4$, D-Phe$^7$]-α-MSH exhibited a "prolonged" biological effect superior to α-MSH and [Nle$^4$]-α-MSH and equivalent to that of heat-alkali treated α-MSH and [Nle$^4$]-α-MSH.

EXAMPLE 5

[Nle$^4$, D-Phe$^7$]-α-MSH was examined for its biological effects on melanosome dispersion in vivo, using the frog (*Rana pipiens*), and the lizard (*Anolis carolinensis*). See, Hadley, et al. Science, 213, pp. 1025-1027 (1981).

Frogs of both sexes were placed in white plastic containers with a small amount of water under overhead illumi-nation. Under these conditions, the animals became light green in color, presumably because they were not releasing any endogenous α-MSH. Forty-eight hours later, light reflectance from the dorsal surface of the animals was measured with a Photovolt reflectometer. At this time, the frogs were injected subcutaneously with Ringer solution (controls) or Ringer solutions containing α-MSH, [Nle$^4$]-α-MSH, or [Nle$^4$, D-Phe$^7$]-α-MSH (100 μl of a $10^{-4}$M solution per 10 g of body weight) to provide a final body concentration of approximately 18 μg/10 g. Subsequent reflectance values were taken at 2- to 3-day intervals for 6 weeks.

Maximum darkening of the frogs was obtained with [Nle$^4$, D-Phe$^7$]-α-MSH; at 6 weeks the frogs injected with the compound still showed half-maximum darkening. In contrast, the darkening effect of α-MSH was transient, being totally lost by 2 days after injection. [Nle$^4$]-α-MSH was effective for only a slightly longer period than α-MSH. A single injection of a lower concentration (0.18 μg/10 g, final body concentration) of [Nle$^4$, D-Phe$^7$]-α-MSH was nearly as effective as the higher dose (18 μg/10 g).

A single injection of [Nle$^4$, D-Phe$^7$]-α-MSH (18 μg/10 g, final body concentration) into the lizard (*A. carolinensis*) also caused a prolonged darkening (about 3 days) of the skin compared to the effect of either α-MSH or [Nle$^4$]-α-MSH.

The following example relates to determination of resistence to serum proteoytic enzymes degradation of the compound of Example 1.

EXAMPLE 6

Synthetic α-MSH, [Nle$^4$]-α-MSH and [Nle$^4$, D-Phe$^7$]-α-MSH were incubated (37° C.) under sterile conditions in Corning flasks containing Ham's F-10 media containing 10% horse serum and 2% fetal calf serum. Samples of the media containing the peptides (10 nM) were removed at time zero and at 24, 48 and 72 hours. The samples were immediately frozen and assayed for biological activity using the in vitro frog skin bioassay.

Figure 3:
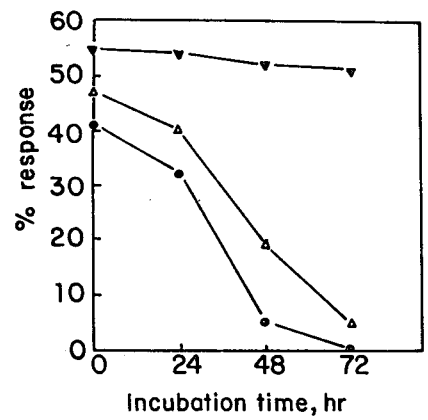

As illustrated in FIG. 3, [Nle$^4$, D-Phe$^7$]-*a*-MSH, (▼) was almost totally resistant to loss of biological activity while both *a*-MSH, (●) and [Nle$^4$]-*a*-MSH, (△) lost essentially all biological activity over this time period.

EXAMPLE 7

The procedures of Hunter, et al., Nature, 194, pp. 495-496 (1962) were applied to [Nle$^4$, D-Phe$^7$]-α-MSH and the resultant compound was tested for adenylate cyclase activity as in Example 2. Unlike α-MSH (which loses biological activity upon Oxidative iodination) or [Nle$^4$]-α-MSH (which retains activity after Chloramine-T treatment, but loses activity upon subsequent exposure to sodium iodide) the compound of Example 1 was iodinated through use of lacto peroxidase or iodogen and fully retained its activity.

In summary, the foregoing Examples 2 through 7 demonstrate that [Nle$^4$, D-Phe$^7$]-α-MSH according to the present invention: (a) possesses more potent adenylate cyclase activity than either the natural hormone or the most potent prior art synthetic analogue; (b) possesses more potent tyrosinase activity than α-MSH or [Nle$^4$]-α-MSH; (c) possesses more prolonged ability to stimulate melanosome dispersion in vitro and in vivo than either the natural hormone or the [Nle$^4$] analogue (equivalent to the less potent heat-alkali treated forms of these compounds); (d) has greater stability toward degradation by serum proteolytic enzymes than either α-MSH or its [Nle$^4$] analogue; and, (e) substantially retains biological activity when iodinated.

While [Nle$^4$, D-Phe$^7$]-α-MSH according to Example 1 is clearly the presently most preferred and thoroughly tested compound of the invention, it is believed that equivalent advantageous properties are possessed by other synthetic analogues of the invention wherein an amino acid in D-isomeric configuration other than phenylalanine is provided at position 7 in the tridecapeptide. In this regard, it is expected that substitution of aromatic amino acids such as tyrosine and heterocyclic amino acids such as tryptophan will, owing to their structural similarity to phenylalanine, exhibit equivalent activity.

Similarly, tridecapeptides comprehended by the present invention include not only those having the native methionine residue or norleucine residue at position 4 but also those including other amino acids, especially the aliphatic amino acids such as leucine, isoleucine, and valine, at that position. Owing to the apparent greater likelihood of oxidative degradation of sulfur-containing amino acid residues in the course of standard iodination procedures, compounds of the invention having methionine, cysteine and cystine residues at position 4 are not expected to withstand Chloramine-T and sodium iodide treatment as well as analogues with aliphatic amino acids at that position.

The following example illustrates preparation of certain compounds of the invention.

EXAMPLE 8

Employing the method of Example 1, the following tridecapeptides of the invention may be prepared which: (a) incorporate phenylalanine in D-isomeric configuration at position 7; (b) incorporate either the native methionine or a representative aliphatic amino acid residue at position 4; and (c) additionally include an amino acid residue of D-isomeric configuration at a position other than position 7.

[D-Ser$^1$, D-Phe$^7$]-α-MSH;
[D-Tyr$^2$, D-Phe$^7$]-α-MSH;
[D-Ser$^3$, D-Phe$^7$]-α-MSH;
[D-Met$^4$, D-Phe$^7$]-α-MSH;
[D-Glu$^5$, D-Phe$^7$]-α-MSH;

[D-His⁶, D-Phe⁷]-α-MSH;
[D-Phe⁷, D-Arg⁸]-α-MSH;
[D-Phe⁷, D-Trp⁹]-α-MSH;
[D-Phe⁷, D-Lys¹¹]-α-MSH;
[D-Phe⁷, D-Pro¹²]-α-MSH;
[D-Phe⁷, D-Val¹³]-α-MSH;
[D-Ser¹, Nle⁴, D-Phe⁷]-α-MSH;
[D-Tyr², Nle⁴, D-Phe⁷]-α-MSH;
[D-Ser³, Nle⁴, D-Phe⁷]-α-MSH;
[Nle⁴, D-Glu⁵, D-Phe⁷]-α-MSH;
[Nle⁴, D-His⁶, D-Phe⁷]-α-MSH;
[Nle⁴, D-Phe⁷, D-Arg⁸]-α-MSH:
[Nle⁴, D-Phe⁷, D-Trp⁹]-α-MSH;
[Nle⁴, D-Phe⁷, D-Lys¹¹]-α-MSH;
[Nle⁴, D-Phe⁷, D-Pro¹²]-α-MSH;
[Nle⁴, D-Phe⁷, D-Val¹³]-α-MSH

It is apparent from the above that any of the amino acid residues of the native tridecapeptide hormone which are present in the naturally occurring L-isomeric configuration may be provided in synthetic compounds of the invention in D-isomeric form except for glycine, which does not admit to such configuration.

The procedures of Example 1 may also be employed in the preparation of tridecapeptides of the invention which include two or three amino acid residues in D-isomeric configuration in addition to the residue at position 7.

On the basis of the prior observation of diminished potency of [D-Ser¹]-α-MSH and [D-Tyr²]-α-MSH, it might be expected that compounds of the invention incorporating D-isomeric configuration serine and tyrosine residues at positions 1 and 2 may display somewhat diminished potency but should nonetheless possess the prolonged biological activity of compounds having a D-isomeric configuration amino acid residue in position 7.

The remarkable properties of compounds of the invention render them exceptionally useful as substitutes for α-MSH and [Nle⁴]-α-MSH in existing diagnostic, therapeutic and basic research schemes. In the area of diagnostic procedures, it is apparent that compounds of the invention, expecially those which have been radioiodinated or coupled with gamma radiation emitters, are exceptionally well suited for use in locating and/or differentially characterizing melanoma cells on the basis of association with melanotropin receptors in such cells. The serum stability of compounds of the invention makes them prime candidates in proposed selective drug delivery systems wherein target tissues are known to have high concentrations of melanotropin receptors. The relative high potency and prolonged activity of compounds of the invention in color change-associated phenomena is expected to be duplicated in the context of other biological effects (such as central nervous system effects) previously noted for naturally occurring melanocyte stimulating hormone and its synthetic analogues.

What is claimed is:

1. A tridecapeptide of the formula:

Ac-Ser¹-Tyr²-Ser³-Y⁴-Glu⁵-His⁶-X⁷-Arg⁸-Trp⁹-Gly¹⁰-Lys¹¹-Pro¹²-Val¹³-NH₂

X is D-phenylalinine Y is methionine or norleucine, and all remaining amino acid residues in said tridecapeptide are in L-isomeric configuration.

2. A tridecapeptide according to claim 1 which is [D-Phe⁷]-α-MSH.

3. A tridecapeptide according to claim 1 which is [Nle⁴, D-Phe⁷]-α-MSH.

* * * * *